United States Patent
Saxena et al.

(10) Patent No.: US 11,879,825 B2
(45) Date of Patent: *Jan. 23, 2024

(54) METHOD FOR DIGITALLY CHARACTERIZING THE PERMEABILITY OF ROCK

(71) Applicant: SHELL OIL COMPANY, Houston, TX (US)

(72) Inventors: Nishank Saxena, Houston, TX (US); Amie Marie Hows, Houston, TX (US); Ronny Hofmann, Houston, TX (US); Matthias Appel, Houston, TX (US); John Justin Freeman, Houston, TX (US)

(73) Assignee: SHELL USA, INC., Houston, TX (US)

( * ) Notice: Subject to any disclaimer, the term of this patent is extended or adjusted under 35 U.S.C. 154(b) by 431 days.

This patent is subject to a terminal disclaimer.

(21) Appl. No.: 17/414,421

(22) PCT Filed: Dec. 16, 2019

(86) PCT No.: PCT/US2019/066539
§ 371 (c)(1),
(2) Date: Jun. 16, 2021

(87) PCT Pub. No.: WO2020/131694
PCT Pub. Date: Jun. 25, 2020

(65) Prior Publication Data
US 2022/0099551 A1 Mar. 31, 2022

Related U.S. Application Data

(60) Provisional application No. 62/781,019, filed on Dec. 18, 2018.

(51) Int. Cl.
*G01N 15/08* (2006.01)
*G06T 7/11* (2017.01)
(Continued)

(52) U.S. Cl.
CPC ........... *G01N 15/08* (2013.01); *G01N 23/046* (2013.01); *G01N 23/083* (2013.01); *G01N 33/24* (2013.01);
(Continued)

(58) Field of Classification Search
CPC .... G01N 15/08; G01N 23/046; G01N 23/083; G01N 33/24; G01N 2015/0846;
(Continued)

(56) References Cited

U.S. PATENT DOCUMENTS 8,311,788 B2 11/2012 Hurley et al.
9,070,049 B2 6/2015 Fredrich et al.
(Continued)

FOREIGN PATENT DOCUMENTS

WO 2014142976 A1 9/2014

OTHER PUBLICATIONS

Hussain, Furqan, et al. "Computation of relative permeability from imaged fluid distributions at the pore scale." Transport in porous media 104 (2014): 91-107.*
(Continued)

*Primary Examiner* — Xuemei G Chen
(74) *Attorney, Agent, or Firm* — SHELL USA, INC.

(57) ABSTRACT

The present invention provides a method for estimating the permeability of rock from a digital image of the rock. A three-dimensional image of a rock is obtained and segmented, and an image permeability is determined from the segmented image of the rock. Permeability correction factors are obtained from the segmented image and from a non-wetting liquid capillary pressure curve derived from the segmented image, and the permeability correction parameters are applied to the image permeability to obtain a corrected image permeability of the rock.

16 Claims, 4 Drawing Sheets

(51) Int. Cl.
  *G01N 23/046* (2018.01)
  *G01N 23/083* (2018.01)
  *G01N 33/24* (2006.01)

(52) U.S. Cl.
  CPC ........ *G06T 7/11* (2017.01); *G01N 2015/0846* (2013.01); *G01N 2223/04* (2013.01); *G01N 2223/419* (2013.01); *G01N 2223/616* (2013.01); *G06T 2207/10081* (2013.01); *G06T 2207/20081* (2013.01); *G06T 2207/30181* (2013.01)

(58) Field of Classification Search
  CPC ......... G01N 2223/04; G01N 2223/419; G01N 2223/616; G01N 2223/305; G01N 15/088; G06T 7/11; G06T 2207/10081; G06T 2207/20081; G06T 2207/30181; G06T 2207/20084
  See application file for complete search history.

(56) References Cited

U.S. PATENT DOCUMENTS

| | | | |
|---|---|---|---|
| 9,134,457 B2 | 9/2015 | Hurley et al. | |
| 9,558,588 B2 * | 1/2017 | Koroteev | G06T 5/40 |
| 10,466,386 B2 | 11/2019 | Hurley | |
| 10,514,372 B2 * | 12/2019 | De Prisco | G01N 15/08 |
| 11,010,883 B2 * | 5/2021 | Anifowose | G06F 18/23 |
| 2006/0116828 A1 * | 6/2006 | Chen | G01R 33/44 73/866 |
| 2011/0066404 A1 | 3/2011 | Salazar-Tio et al. | |
| 2012/0275658 A1 | 11/2012 | Hurley et al. | |
| 2013/0018641 A1 | 1/2013 | Prisco et al. | |
| 2013/0308831 A1 * | 11/2013 | Dvorkin | G01N 33/24 382/109 |
| 2014/0002081 A1 * | 1/2014 | Mitchell | G01N 15/088 324/309 |
| 2014/0044315 A1 | 2/2014 | Derzhi et al. | |
| 2015/0043787 A1 | 2/2015 | Fredrich et al. | |
| 2015/0331145 A1 * | 11/2015 | Grachev | G06T 17/05 703/2 |
| 2016/0379356 A1 * | 12/2016 | Louis | G01N 15/088 382/109 |
| 2017/0132781 A1 * | 5/2017 | Roth | G01N 15/08 |
| 2017/0363531 A1 * | 12/2017 | Hruska | G01V 3/38 |
| 2018/0018561 A1 * | 1/2018 | Hassan | G06N 3/086 |
| 2018/0033167 A1 * | 2/2018 | Moreaud | G06T 7/136 |
| 2018/0121579 A1 | 5/2018 | Fredrich et al. | |
| 2018/0321127 A1 | 11/2018 | León Carrera et al. | |
| 2019/0050508 A1 * | 2/2019 | Crouse | G06F 30/23 |
| 2019/0154597 A1 * | 5/2019 | Zhang | G01N 15/088 |
| 2020/0005013 A1 * | 1/2020 | Zhao | G06V 20/695 |
| 2020/0333234 A1 * | 10/2020 | Al Marzouqi | G01N 33/24 |

OTHER PUBLICATIONS

Chauhan, Swarup, et al. "Processing of rock core microtomography images: Using seven different machine learning algorithms." Computers & Geosciences 86 (2016): 120-128.*
Wu, Jinlong, Xiaolong Yin, and Heng Xiao. "Seeing permeability from images: fast prediction with convolutional neural networks." Science bulletin 63.18 (2018): 1215-1222.*
International Search Report and Written Opinion received for PCT Patent Application No. PCT/US2021/028299, dated Aug. 24, 2021, 12 pages.
Hilpert et al., "Pore-morphology-based Simulation of Drainage in Totally Wetting Porous Media", Advances in Water Resources, Feb.-Mar. 2001, vol. 24, Issue No. 3-4, pp. 243-255.
Alpak et al., "Prediction of Fluid Topology and Relative Permeability in Imbibition in Sandstone Rock by Direct Numerical Simulation", Advances in Water Resources, Dec. 2018, vol. 122, pp. 49-59.
Alpak et al., "Direct Simulation of Pore-scale Two-phase Viscocapillary Flow on Large Digital Rock Images Using a Phase-field Lattice Boltzmann Method on General-purpose Graphics Processing Units", Computational Geosciences, Oct. 1, 2019, vol. 23, Issue No. 5, pp. 849-880.
Dvorkin et al., "Etudes in Computational Rock Physics: Alterations and Benchmarking", Geophysics, vol. 77, Issue No. 3, Jun. 2012, pp. D45-D52.
Fredrich et al., "Digital Rocks: Developing an Emerging Technology Through to a Proven Capability Deployed in the Business", Journal of Petroleum Technology, Oct. 27, 2014, pp. 2383-2399.
International Search Report and Written Opinion received for PCT Patent Application No. PCT/US2019/066539, dated Apr. 1, 2020, 13 pages.
Amabeoku et al. "Evaluation and Application of Digital Rock Physics (DRP) for Special Core Analysis in Carbonate Formations", International Petroleum Technology Conference, Mar. 28, 2013, pp. 26-28, XP055580402.
Saxena et al., "Imaging and Computational Considerations for Image Computed Permeability: Operating Envelope of Digital Rock Physics", Advances in Water Resources, vol. 116, Apr. 4, 2018, pp. 127-144, XP085402086.
Saxena et al., "Rock Properties From Micro-ct Images: Digital Rock Transforms for Resolution, Pore Volume and Field of View", Advances in Water Resources, vol. 134, Sep. 10, 2019, 13 pages, XP085905530.
Budakov et al., "Driving Digital Rock Towards Machine Learning: Predicting Permeability With Gradient Boosting and Deep Neural Networks", Mar. 16, 2018, pp. 1-15, XP055678933.
Otsu, "A Threshold Selection Method from Gray-level Histogram", IEEE, Trans. SMC-9, 1979, pp. 62-66.
Chuang et al., "Fuzzy C-Means Clustering with Spatial Information for Image Segmentation", Comput. Med. Imaging Graph, vol. 30, 2006, pp. 9-15.
Zecevic et al., "Progress in Electron Tomography to Assess the 3d Nanostructure of Catalysts", Current Opinion in Solid State and Materials Science, vol. 17, 2013, pp. 115-125.
Saxena et al., "Estimating Pore Volume of Rocks from Pore-Scale Imaging", Transport in Porous Media, vol. 129, Issue No. 1, May 11, 2019, pp. 403-419.
International Search Report and Written Opinion received for PCT Patent Application No. PCT/US2020/064180, dated Mar. 16, 2021, 11 Pages.
International Search Report and Written Opinion received for PCT Patent Application No. PCT/US2019/066543, dated Apr. 1, 2020, 13 Pages.
Saxena et al., "Effect of Image Segmentation & Voxel Size on Micro-CT Computed Effective Transport & Elastic Properties", Marine and Petroleum Geology, vol. 86, Sep. 1, 2017, pp. 972-990.
Garba et al., "Electrical Formation Factor of Clean Sand From Laboratory Measurements and Digital Rock Physics", Solid Earth Discuss, vol. 10, Issue No. 5, Jan. 1, 2019, pp. 1505-1517, XP055781308.
Lin et al., "Quantification of Sub-resolution Porosity in Carbonate Rocks by Applying High-salinity Contrast Brine Using X-ray Microtomography Differential Imaging", Advances in Water Resources, vol. 96, Aug. 3, 2016, pp. 306-322, XP029723812.
Saxena et al., "Estimating Electrical Cementation and Saturation Exponents Using Digital Rock Physics", Journal of Petroleum Science and Engineering, vol. 198, Dec. 3, 2020, XP086434571.
Archie, "Classification of Carbonate Reservoir Rocks and Petrophysical Considerations", Bulletin of the American Association of Petroleum Geologists, vol. 36, Issue No. 2, Feb. 1, 1952, pp. 278-298.
Archie, "The Electrical Resistivity Log as an Aid in Determining Some Reservoir Characteristics", Transactions of the AIME, vol. 146, Issue No. 1, Dec. 1942, pp. 54-62.
Garboczi, "Finite Element and Finite Difference Programs for Computing the Linear Electric and Elastic Properties of Digital Images of Random Materials", NISTIR 6269, Dec. 1, 1998, 213 Pages.

(56) References Cited

OTHER PUBLICATIONS

Andra et al., "Digital Rock Physics Benchmarks—Part II: Computing Effective Properties", Computers and Geosciences, vol. 50, Jan. 2013, pp. 33-43.

* cited by examiner

METHOD FOR DIGITALLY CHARACTERIZING THE PERMEABILITY OF ROCK

CROSS REFERENCE TO RELATED APPLICATIONS

This is a National stage application of International application No. PCT/US2019/066539 filed 16 Dec. 2019, which claims priority of U.S. Provisional application No. 62/781,019, filed 18 Dec. 2018, which is incorporated herein by reference in its entirety.

FIELD OF THE INVENTION

The present invention relates to a method of characterizing the permeability of rock. In particular, the present invention relates to a method of characterizing the permeability of a rock from a three-dimensional image of the rock.

BACKGROUND OF THE INVENTION

Accurate determination of petrophysical characteristics of rock such as porosity and permeability within a hydrocarbon-containing reservoir is important in determining whether to select the hydrocarbon-containing reservoir for development, as well as developing and managing the hydrocarbon-containing reservoir. For example, overestimating the absolute permeability (hereinafter the "permeability") of the rock of a hydrocarbon-containing formation may lead to significant overestimation of fluid flow through the formation and, therefore, overestimation of the quantity of hydrocarbon fluids that may be produced from the formation. Overestimation of the permeability of the rock of a hydrocarbon-containing formation may lead to improper spacing of wells, or, in a worst-case scenario, the development of a formation that may not provide adequate commercial production of hydrocarbons.

Traditionally, petrophysical characteristics of hydrocarbon-containing formation rock have been determined by physical testing of rock samples. Such tests, however, require substantial time and are quite expensive. Further, the number of samples that may be processed is relatively limited due to the time and expense required to conduct each test.

Digital rock physics is a technology that has been developed to provide faster, more, and less expensive analysis of hydrocarbon-containing formation rocks to determine key petrophysical characteristics of the rocks. Digital rock physics utilizes digital images of formation rocks to simulate rock multiphysics at the pore scale and predict properties of complex rocks.

Permeability is among the most fundamental of rock properties and is utilized to determine the propensity of a fluid to flow through a hydrocarbon-containing formation such that the fluid may be produced from the formation. Current digital rock physics technologies determine the permeability of a rock sample by capturing a three-dimensional image of the rock, for example by 3-D x-ray computer tomography, segmenting the resulting image into solid and void space voxels utilizing various image segmentation algorithms, and running a computational simulation of fluid dynamics in the segmented rock image to determine the permeability of the rock.

Figure 1:
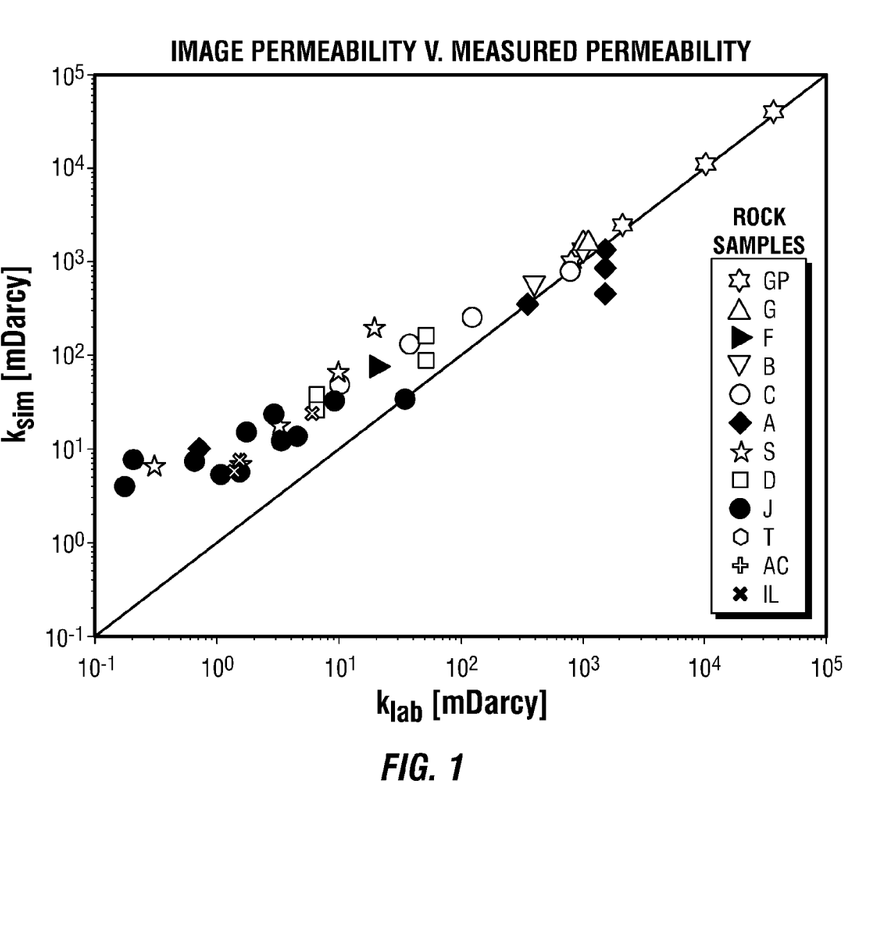
FIG. 1 is a graph showing a plot of laboratory measured permeability of rocks v. the image permeability as determined by digital rock image methods of the prior art.

Current digital rock physics methods for determining the permeability of a rock, however, exhibit a significant systematic offset between laboratory measurements of permeability and permeability computed using digital rock physics models. Permeability computed using digital rock physics models is consistently significantly overestimated, by up to a factor of 10, relative to the permeability as measured by laboratory measurements (the "true" permeability) in rocks having a true permeability of smaller than 100 mDarcy. This offset is shown graphically in FIG. 1 where permeability computed using conventional digital rock physics models (ksim) is plotted against laboratory measured "true" permeability (klab). The digital rock physics models consistently overestimate the image permeability relative to true permeability at permeabilities of less than 100 mDarcy as shown by the image permeabilities consistently falling above the x=y slope (at which image modelled permeability would equal laboratory measured true permeability) at permeabilities of less than 100 mDarcy.

This bias cannot be accounted for by differences in rock microstructures generated by various segmentation algorithms since such differences are relatively minor as long as all phases are segmented consistently. As such, current digital rock methods are relatively inaccurate and overestimate the true permeability of hydrocarbon-containing formation rock.

An improved digital rock physics method is desirable for more accurately estimating the permeability of hydrocarbon-containing formation rock from a three-dimensional image of the rock.

SUMMARY OF THE INVENTION

According to one aspect of the present invention, there is provided a method for estimating the permeability of a rock, comprising: obtaining a three-dimensional image of a rock wherein the image is comprised of a plurality of voxels and the image has a resolution; processing the three-dimensional image of the rock to segment the image by selecting each voxel of the image to represent either pore space in the rock or solid material in the rock; determining an image permeability of the rock from the segmented three-dimensional image of the rock; deriving a non-wetting liquid capillary pressure curve from the segmented three-dimensional image of the rock; determining one or more permeability correction factors from the segmented three-dimensional image of the rock and the non-wetting liquid capillary pressure curve; and applying the one or more permeability correction factors to the image permeability of the rock to obtain a corrected permeability of the rock.

According to another aspect of the present invention, there is provided a backpropagation-enabled method for estimating the permeability of rock from a three-dimensional image of rock, comprising the steps of: obtaining a three-dimensional image of rock, the three-dimensional image having a resolution; applying a backpropagation-enabled trained model to segment the three-dimensional image of rock; determining an image permeability of the rock from the segmented image; deriving a non-wetting liquid capillary pressure curve from the segmented image; determining one of more permeability correction factors from the non-wetting liquid capillary pressure curve and the resolution; and applying the one or more permeability correction factors to the image permeability of the rock to obtain a corrected permeability of the rock.

According to a further aspect of the present invention, there is provided a backpropagation-enabled method for estimating the permeability of rock from an image of rock, comprising the steps of: obtaining an image of rock, the image selected from the group consisting of a series of 2D projection images, three-dimensional reconstructed images and combinations thereof; and applying a backpropagation-enabled trained model to obtain a permeability of the rock.

BRIEF DESCRIPTION OF THE DRAWINGS

The present invention will be better understood by referring to the following detailed description of preferred embodiments and the drawings referenced therein, in which.

DETAILED DESCRIPTION OF THE INVENTION

The present invention provides a method for accurately estimating the permeability of a rock based on an original three-dimensional pore-scale image of the rock having limited resolution relative to the actual pore structure of the rock. It has been found that, contrary to current assumptions in digital rock physics modelling, that a substantial fraction of the pore volume of hydrocarbon-containing rocks is contained in pores of a size below the image resolution provided by three-dimensional pore-scale imaging technology commonly used to provide images of such rocks. As a result, conventional digital rock physics modelling substantially overestimates the permeability of hydrocarbon-containing rocks having true permeability of less than 100 mDarcy by failing to account for pores that are smaller than the image resolution of the pore-scale imaging technology in the permeability computation.

The present invention provides a method for estimating the permeability of a hydrocarbon-containing rock based upon a three-dimensional digital image provided by pore-scale imaging technology, where the permeability estimated in accordance with the present method includes the permeability provided by pores having a size below the image resolution of the image. The relation between the fraction of permeability that may be estimated from pores visible in an image and the true permeability is estimated using the seemingly unrelated physical mechanism of capillary pressure in rocks. Capillary pressure is the pressure difference across the interface between two immiscible fluids in a constricted channel (e.g. air and a non-wetting liquid such as mercury). Non-wetting liquid injection capillary pressure curves describe the relation between the pressure applied on the non-wetting liquid to overcome capillary pressure and thereby enter pore throats and the fractional bulk volume of the rock that is occupied by the non-wetting liquid at that pressure. The true permeability of a hydrocarbon-containing rock may be estimated by utilizing capillary pressure curves based on an image of a rock to determine a one or more permeability correction factors to be applied to a permeability computationally simulated from visible pores in the image.

The present invention also provides a backpropagation-enabled method for estimating the permeability of rock from a three-dimensional image of rock. A backpropagation-enabled trained model is applied to a three-dimensional image to segment the three-dimensional image of rock.

In a preferred embodiment, the trained model is produced by providing a training set of images of rock, segmenting the images into a plurality of labeled voxels, the plurality of labeled voxels representing pore spaces and solid material in the rock, and using the labeled voxels to train a model via backpropagation.

The training set of images of rock may include, for example, 2D projection images obtained from a pore-scaling imaging technology, 3D images reconstructed from 2D projection images, synthetic 2D images, synthetic 3D images, and combinations thereof. In a preferred embodiment, the training set of images is obtained from a cloud-based tool adapted to store 2D projection images from a pore-space imaging technology, especially micro-CT and thin sections. The tool is adapted to process the 2D projection images to produce a reconstructed 3D image. The tool is also adapted to store the resulting 3D images.

Examples of backpropagation-enabled processes include, without limitation, artificial intelligence, machine learning, and deep learning. It will be understood by those skilled in the art that advances in backpropagation-enabled processes continue rapidly. The method of the present invention is expected to be applicable to those advances even if under a different name. Accordingly, the method of the present invention is applicable to the further advances in backpropagation-enabled processes, even if not expressly named herein.

A preferred embodiment of a backpropagation-enabled process is a deep learning process, including, but not limited to a convolutional neural network.

The backpropagation-enabled process may be supervised, semi-supervised, unsupervised or a combination thereof. In one embodiment, a supervised process is made semi-supervised by the addition of an unsupervised technique.

In a supervised backpropagation-enabled process, the training set of images is labeled to provide examples of pore spaces and solid material of interest. In an unsupervised backpropagation-enabled process, a pore space and/or solid material of interest may be identified by, for example, drawing a polygon around the image of interest in the image. The trained process will then identify areas of interest having similar latent space characteristics. When the training set is labeled images, the labels may have a dimension of 1D-3D.

In one embodiment, the supervised backpropagation-enabled process is a classification process. The classification process may be conducted voxel-wise, slice-wise and/or volume-wise.

In another embodiment, the unsupervised backpropagation-enabled process is a clustering process. The clustering process may be conducted voxel-wise, slice-wise and/or volume-wise.

In another embodiment, the unsupervised backpropagation-enabled process is a generative process. The generative process may be conducted voxel-wise, slice-wise and/or volume-wise.

Preferably, the backpropagation-enabled process is a segmentation process.

In a preferred embodiment, the training step includes validation and testing.

In the method of the invention, petrophysical characteristics of a rock, particularly the permeability of the rock, may be estimated from a three-dimensional image of the rock. In a preferred embodiment, the rock may be a rock from any hydrocarbon-containing formation, or a portion of a hydrocarbon-containing formation, for which the petrophysical characteristics of the formation, or portion thereof, are of interest. Preferably, the rock may be a sandstone, a carbonate, a shale, and combinations thereof from a hydrocarbon-containing formation. The rock may be obtained by conventional means for obtaining rock samples from a hydrocarbon formation. In a preferred embodiment, a core sample of the rock is obtained by coring a portion of the formation from within a well in the formation. Alternatively, a sample of the rock may be obtained from drill cuttings produced in drilling a well in the formation.

The rock sample should be of sufficient size to obtain a three-dimensional image of sufficient volume at the scale that the image is generated. In particular, the rock sample should be of sufficient size such that permeability characteristics of the bulk of the sample predominate over the permeability characteristics of the edges of the sample at the scale or field of view of the image to be generated.

A three-dimensional image comprised of a plurality of voxels is obtained from the rock sample. The three-dimensional image of the rock may be obtained utilizing pore-scale imaging technology. A three-dimensional image of the rock may be obtained by x-ray computer tomography, including, without limitation, x-ray micro-computed tomography (micro-CT) and x-ray nano-computed tomography (nano-CT), acoustic microscopy, or magnetic resonance imaging. Most preferably the three-dimensional image of the rock is obtained by micro-CT to provide sufficient field of view of the rock to avoid edge pores distorting the overall porosity, pore throat size, and permeability of the resulting image, as well as to reduce scanning time and computational requirements that higher resolution tomography (e.g. nano-CT) would require.

In a preferred embodiment, the three-dimensional image is obtained from a cloud-based tool adapted to store 2D projection images from a pore-space imaging technology, especially micro-CT and thin sections. The tool is adapted to process the 2D projection images to produce a reconstructed 3D image. The tool is also adapted to store the resulting 3D images.

The three-dimensional image of the rock obtained by pore-scale imaging technology has a resolution. The voxels of the three-dimensional image define the resolution of the image. The image is comprised of a plurality of voxels, where the volume defined by each voxel represents a maximum resolution of the image. The resolution of the image should be selected to provide a voxel size at which the dominant pore throats for fluid flow in the rock are sufficiently resolved and at which a sufficient field of view is provided so as to be representative of the whole rock for a given petrophysical property to be analyzed (e.g. permeability). For purposes herein, the dominant pore throat size (Da) is the size of pore throats of pores that a non-wetting liquid enters at the pore entry pressure (Pd), where the pore entry pressure is the minimum pressure required before the non-wetting liquid can begin to invade the pore structure of the rock.

The resolution of a micro-CT image may be chosen based on the size of the rock sample, the relative average pore size of the type of rock, the time required for the imaging, and the computational power required to store and conduct further computational activity on the image data. The image resolution is chosen to be detailed enough that a non-wetting liquid capillary injection curve can be plotted based on a segmented image produced from the image while maintaining a sufficient field of view to avoid edge pores distorting the overall porosity, pore throat size, and permeability of the resulting image. In a preferred embodiment, the image resolution is selected to require as little computational power to store and conduct further computational activity on the image while providing sufficient detail to construct a capillary injection curve based on the segmented image. The image resolution may be selected based on the type of rock, where sandstones generally have a larger pore structure than carbonates, and require less image resolution than carbonates, and carbonates have a larger pore structure than shales, and require less image resolution than shales. The resolution of the micro-CT image may range from 0.1 $\mu m^3$ to 30 $\mu m^3$ per voxel. For sandstones, the micro-CT image preferably is produced at a resolution of from 1 $\mu m^3$ to 25 $\mu m^3$ per voxel, or from 2.5 $\mu m^3$ to 15 $\mu m^3$ per voxel; for carbonates the resolution of the micro-CT image may range from 0.5 $\mu m^3$ to 20 $\mu m^3$, or from 1 $\mu m^3$ to 10 $\mu m^3$; and for shales the resolution of the micro-CT (or nano-CT) image may range from 0.1 $\mu m^3$ to 10 $\mu m^3$, or from 0.5 $\mu m^3$ to 5 $\mu m^3$.

In a preferred embodiment, the acquired image may be processed to reduce noise and image artifacts. Noise may be filtered from the acquired image by filtering using a local means filter to reduce noise Imaging artifacts, predominant at the outer edges of the acquired image, may be reduced by processing the image while excluding the outer edges of the image.

The three-dimensional image obtained of the rock is processed to segment the voxels of the image into voxels representing either pore space in the rock or solid material in the rock, thereby producing a binary image in which pore voxels have a value of 0 and solid material voxels have a value of 1 (or vice versa). The image obtained of the rock may be a grayscale image, and processing the voxels of the image to segment the image into voxels representing pore space or solid material may be effected by assigning a voxel a designation as pore space or as solid material based on a threshold, wherein voxels having an image intensity above the threshold may be assigned a value representing a pore (or solid material) and voxels having an image intensity below the threshold may be assigned a value representing solid material (or a pore). A threshold may be calculated using Otsu's method as described in Otsu, N., *A Threshold Selection Method from Gray-level Histogram, IEEE* pp. 62-66, *Trans. SMC*-9 (1979), or other threshold calculation algorithms known in the art.

The three-dimensional image of the rock may be processed to segment the voxels into pore space voxels and solid material voxels utilizing segmentation algorithms known in the art. In one embodiment, the image may be segmented using a fuzzy c-means clustering algorithm in accordance with the method as described in Chuang, K.-S., Tzeng, H.-L., Chen, S., Wu, J., Chen, T.-J. *Fuzzy C-Means Clustering with Spatial Information for Image Segmentation, Comput. Med. Imaging Graph.*, 30, 9-15 (2006). In another embodiment, the image may be segmented using an Otsu algorithm. Segmentation using segmentation algorithms is preferably conducted automatically using data processing systems.

After the image has been segmented, an image permeability is determined from the segmented three-dimensional image of the rock. Permeability may be estimated from the segmented three-dimensional image of the rock by computational numerical simulation of fluid flow through the image of the rock. Computational numerical simulation of fluid flow through the image of the rock to determine the image permeability may be conducted using conventional fluid flow simulations. In an embodiment of the present invention, the image permeability is computed from the three-dimensional image of the rock using a Lattice-Boltzmann simulation.

Figure 2:
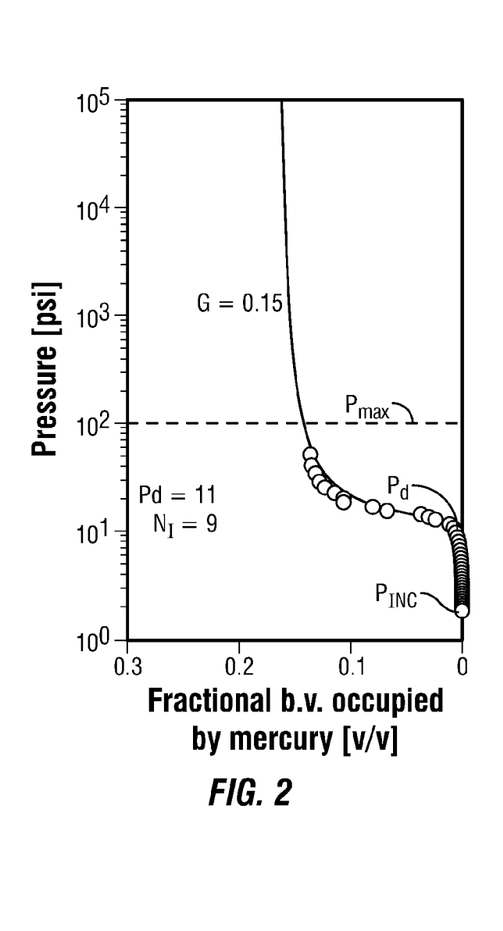
FIG. 2 is a graph of a mercury capillary pressure curve simulated from a digital rock image (porosity occupied by mercury v. pressure)

A non-wetting liquid capillary pressure curve is derived from the segmented three-dimensional image of the rock to provide the dominant pore throat size $D_d$, the pore entry pressure $P_d$, the narrowest constriction of pore bodies at the edge of the image $D_{INC}$, the edge pore body entry pressure $P_{INC}$, and the pore geometric factor curve for use in calculation of one or more permeability correction factors. The non-wetting liquid capillary pressure curve is determined from the segmented three-dimensional image of the rock for pores distinguishable in the segmented image at pressures up to an image-limited pressure. Preferably mercury or Wood's metal is selected as the non-wetting liquid. A non-wetting liquid capillary pressure curve may be determined from the segmented image by plotting the porosity of the rock occupied by the non-wetting liquid at selected pressures up to the image-limiting pressure based upon simulations of the non-wetting liquid filling the pore space of the image. To simulate the non-wetting liquid filling the pore space of the image, the pore throat size penetrated at a given pressure may be determined according to the Young-Laplace equation:

$$D = 4\sigma \cos \theta / P \quad (1)$$

where P is the given pressure, σ is the non-wetting liquid-air surface tension (480 dyne/cm for mercury-air), θ is the contact angle (140° for mercury) and D is the pore throat size penetrated at the given pressure. To evaluate the porosity of the rock occupied by a non-wetting liquid at a given pressure, a simulation may be conducted in which voxels of pore space of pore bodies having a pore throat size of D or larger are assumed to be filled with the non-wetting liquid at the given pressure, the voxels that are "filled" with the liquid are summed, and the porosity of the rock occupied by the non-wetting liquid is calculated by dividing the sum of the number of pore space voxels filled with liquid by the total number of voxels in the image. As shown in FIG. 2, the porosity of the rock occupied by the non-wetting liquid may then plotted against the given pressure for a number of selected given pressures up to the image limited pressure $P_{max}$ to plot the capillary pressure curve and to determine the edge pore body pressure $P_{INC}$ and the pore entry pressure $(P_d)$. The edge pore body pressure $(P_{INC})$ is the pressure at which the non-wetting liquid initially enters pore bodies at the edge of the image, the pore entry pressure $(P_d)$ is the pressure at which the non-wetting liquid initially enters pores in the rock, and the image-limited pressure $(P_{max})$ is the minimum pressure required to overcome the capillary pressure of the narrowest pore throat distinguishable in the segmented image. The dominant pore throat size $D_d$ may be calculated from the pore entry pressure $P_d$ and the narrowest constriction of pore bodies at the edge of the image $D_{INC}$ may be calculated from the edge pore body entry pressure $P_{INC}$ in accordance with equation 1 above.

A corrected image porosity is also estimated for use in calculation of a permeability correction factor. An image porosity of the rock is estimated from the segmented three-dimensional image of the rock. The image porosity of the rock may be determined by summing the number of voxels in the segmented image that represent pore space, summing the total number of voxels in the segmented image (or obtaining the total number of voxels from the imaging parameters), then dividing the sum of the number of voxels in the segmented image that represent pore space by the total number of voxels in the segmented image. A sum of the number of voxels in the segmented image that represent pore space may be determined by adding up the number of voxels assigned a binary value (e.g. 1 or 0) representing pore space. A sum of the total number of voxels in the segmented image may be determined by adding up the total number of voxels assigned a binary value, both pore space voxels and solid material voxels.

A porosity correction factor is determined from the segmented three-dimensional image to correct the image porosity of the rock to obtain a corrected image porosity of the rock. The relation between the image porosity ($\varphi_I$), true porosity ($\varphi_\infty$), and the correction factor (α) may be expressed as follows:

$$\varphi_I = \alpha \varphi_\infty \text{ where } 0 < \alpha < 1. \quad (2)$$

Thomeer's model of the Capillary Pressure Curve provides that:

$$\varphi_P = \varphi_\infty (e^{-G/Log10(N)}) \quad (3)$$

where $\varphi_P$ is the porosity of the rock occupied by a non-wetting liquid at pressure P, $\varphi_\infty$ is the porosity of the rock occupied by a non-wetting liquid at infinite pressure (the true porosity since the pressure is sufficient to force the non-wetting liquid through the smallest pore throat in the rock), G is the pore geometric factor reflecting the distribution of pore throats and their associated pore bodies' volume, and N is the pore throat resolution parameter. The porosity correction factor α, therefore, can be determined from the pore geometric factor G and the image pore throat resolution parameter Nd according to the following equation $$\alpha = e^{-G/Log10(Nsub I)} \quad (4).$$

The image pore throat resolution parameter $N_I$ is determined from the non-wetting liquid capillary pressure curve derived from the image and the image resolution as determined from the size of the voxels. The pore throat resolution parameter $N_I$ is the ratio of the image pore throat size $(D_d)$ entered by the non-wetting liquid at the entry pressure $(P_d)$ to the size of the voxels $(\Delta x)$, $N_I = (D_d/\Delta x)$. The size of the voxels may be determined from the parameters of the three-dimensional imaging (i.e. the resolution of the image). The pore throat size $(D_d)$ of pores entered by the non-wetting liquid at entry pressure $(P_d)$ may be determined from the non-wetting liquid capillary pressure curve derived from the segmented three-dimensional image of the rock according to the equation:

$$D_d = 4\sigma \cos \theta / P_d \quad (5).$$

The pore geometric factor G is determined from the non-wetting liquid capillary pressure curve derived from the image. The pore geometric factor G may be determined by plotting a best fit curve to the non-wetting liquid capillary pressure curve simulated from the segmented image and determining the pore geometric factor from the shape of the curve in accordance with methods known in the art. The best fit curve may be plotted by the least squares method or by any conventional curve-fitting method.

As described above, the pore geometric factor G and the pore throat resolution parameter $N_I$ are utilized to determine the porosity correction factor. The porosity correction factor $\alpha$ may be calculated from the pore geometric factor G and the pore throat resolution parameter $N_I$ according to the equation:

$$\alpha = (e^{-G/Log10(N_I)}) \quad (6).$$

The porosity correction factor $\alpha$ is then applied to the image porosity of the rock to obtain a corrected image porosity. The corrected image porosity ($\varphi_\infty$) may be estimated from the image porosity ($\varphi_I$) of the rock and the porosity correction factor ($\alpha$) according to the following equation:

$$\varphi_I/\alpha = \varphi_\infty \quad (7)$$

One or more correction factors are then determined to correct the image permeability of the rock to obtain a corrected image permeability of the rock. The relation between the image permeability and the corrected image permeability of the rock may be expressed as follows:

$$k_\infty = k_I/(\beta_R \beta_S \beta_V) \quad (8)$$

where $k_\infty$ is permeability at infinite resolution of the image and infinite field of view (the corrected image permeability), $k_I$ is the image permeability, $\beta_R$ is the permeability image resolution correction factor, $\beta_S$ is the permeability image segmentation correction factor, and $\beta_V$ is the permeability field of view correction factor.

The permeability image resolution correction factor $\beta_R$ may be determined based on the image pore throat resolution parameter $N_I$, determined from the non-wetting liquid capillary pressure curve and the voxel size as described above, and the measured pore throat resolution parameter $N_M$. The permeability image resolution correction factor may be determined from the resolution of the image entry pore throat size relative to the measured entry pore throat size in accordance with the following equation:

$$\beta_R = (N_I/N_M)^2. \quad (9)$$

The measured pore throat resolution parameter $N_M$ may be determined by direct physical measurement of the pressure at which a non-wetting liquid penetrates pores of the body of the rock, determination of the measured dominant pore throat size $D_d$ from the measured pressure according to equation 5, and calculation of the measured pore throat resolution parameter from the measured dominant pore throat size $D_d$ and the voxel size ($\Delta x$) by dividing the measured dominant pore throat size by the voxel size $$\left(\frac{Dd}{\Delta x}\right).$$

Alternatively, and preferably, the measured pore throat resolution parameter may be determined based upon estimation of the difference between the image pore throat resolution parameter $N_I$ and the measured pore throat resolution parameter $N_M$ to provide a close approximation of $N_M$ based upon $N_I$. The estimated measured pore throat resolution parameter $N_E$ may be determined by determining the image pore throat resolution parameter and the measured pore throat resolution parameter of several, preferably at least 5 or at least 10, rock samples having a similar pore structure as the rock for which a corrected image permeability is sought at several image resolutions (voxel sizes), for example from 3 to 10; plotting the measured pore throat resolution parameter $N_M$ against the image pore throat resolution parameter $N_I$ for each of the rock samples; deriving a best fit curve for the plotted points, for example by the least squares method; and determining the estimated measured pore throat resolution parameter from the curve. Rock samples having a similar pore structure may be derived from rocks having the same general classification as the rock for which the corrected image permeability is sought: for example, sandstones without substantially unusual pore structures may be used as reference rock samples for sandstone rocks, carbonate rock samples without substantially unusual pore structures may be used as reference rock samples for carbonate rocks, and shale rock samples without substantially unusual pore structures may be used as reference rock samples for shale rocks. The estimated measured pore resolution parameter $N_E$, once determined, may be used as a standard for use in all further image permeability corrections for similar types of rocks. The estimated measured pore throat resolution parameter $N_E$ is a close approximation of the measured pore throat resolution parameter $N_M$ such that the permeability image resolution correction factor $\beta_R$ may be determined by substituting the estimated measured pore throat resolution parameter $N_E$ for the measured pore throat resolution parameter $N_M$ in the calculation of the permeability image resolution factor $\beta_R$:

$$\beta_R \approx (N_I/N_E)^2. \quad (10)$$

An estimated measured pore resolution parameter $N_E$ for sandstones has been calculated to be $$N_{E(sandstone)} = N_I - 2e^{-0.4(N_I - 1)}. \quad (11)$$

Figure 3:
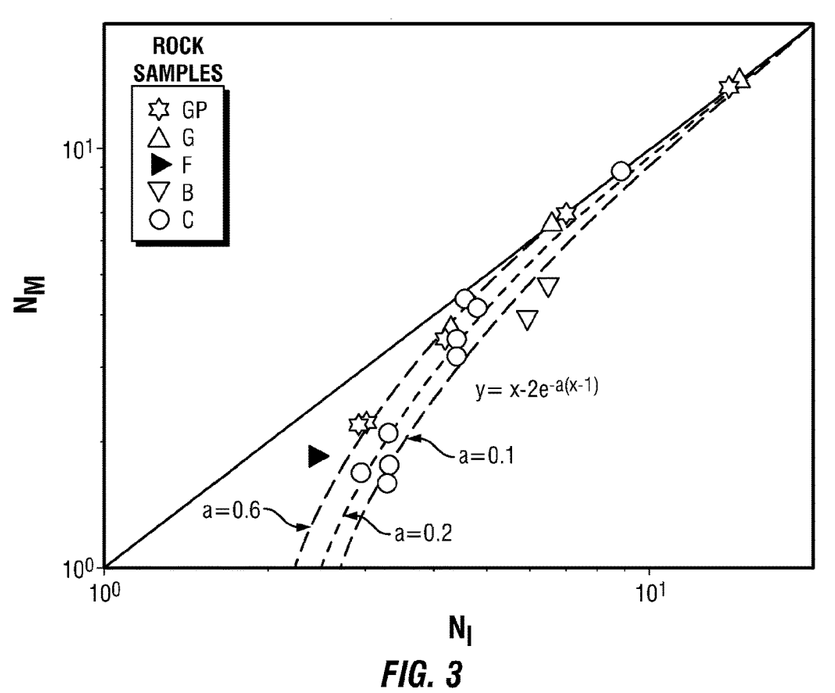
FIG. 3 is a graph showing a plot of measured pore throat resolution parameters against image pore throat resolution parameters for a series of five sandstone rocks at different image resolutions.

A plot of measured pore throat resolution parameters against image pore throat resolution parameters for a series of five sandstone rocks at different image resolutions (voxel sizes, $\Delta x$) is shown in FIG. 3. A best fit curve is plotted through the plotted points, and the best fit curve equation is derived from the bit fit curve to arrive at equation (12) for sandstones, where $y = N_M \approx N_{E(sandstone)}$ and $x = N_I$. For sandstones, then the permeability image resolution correction factor $\beta_{R(sandstone)}$ may be calculated according to the equation:

$$\beta_{R(sandstone)} = \left(\frac{N_I}{N_I - 2e^{-0.4(N_I - 1)}}\right)^2. \quad (12)$$

Similar permeability image resolution correction factors for carbonate rocks and for shale rocks may be determined in a similar manner.

The permeability field of view correction factor $\beta_V$ accounts for the relative contribution of pore structures at the edge of the image to image permeability relative to the overall contribution of all pores to the image permeability. Volumetric contributions of edge pore structures are negligible compared to the total pore volume in permeability measurements based on physical samples of rock due to the sample size of the rock. Permeability measurements based on a digital image may be significantly affected by the volumetric contributions of edge pore structures, particularly in high resolution, low field of view images—where higher resolution and smaller field of view images may have a larger contribution from edge pores. At Representative Elementary Volume (REV) a digital image has sufficient size to capture a sufficient number of grains (solid voxels) to sufficiently sample heterogeneity of the rock, however, due to constraints of image resolution and imaging technology the digital image may not achieve REV. The permeability field of view correction factor $\beta_V$ may be used to correct permeability imprecision due to a digital image not having sufficient size to provide REV.

The permeability field of view correction factor $\beta_V$ may be determined from the relative contribution of pores within the body of the image having an image entry pore throat resolution of $N_I$, the relative contribution of pores at the edges of the image having the narrowest constriction of edge pore body size (DING) to image voxel size ($\Delta x$)–$N_{INC}$, and coefficient p determined as described below. The permeability field of view correction factor $\beta_V$ may be determined in accordance with the following equation:

$$\beta_V = \left(\frac{N_I}{N_{INC}}\right)^{2p} \quad (13)$$

where p may be determined from parameters that may be extracted from the three-dimensional segmented image of the rock. It has been found that the following empirical relation describes the variation of the parameter p:

$$p = \sqrt{1 - e^{-a(D_d \phi_\infty N_{REV}^{0.5})^{-2}}} \quad (14)$$

where $\alpha=0.5$, $D_d$ is the dominant pore throat size calculated from the non-wetting liquid capillary pressure curve as described above, $\varphi_\infty$ is the corrected porosity calculated as described above, and $N_{REV}$ may be calculated according to the formula $N_{REV}=M\times\Delta x/D_{eff}$, where M is the length of the image in voxels along any one axis of the image, $\Delta x$ is the size of a voxel, and $D_{eff}$ is the effective grain size. In order to determine the effective grain size $D_{eff}$, a watershed segmentation may be conducted on the three-dimensional segmented image and the effective grain size determined from the watershed segmented image in accordance with conventional methods known in the art. Alternatively, the effective grain size may also be determined for sandstones according to the following empirical relation:

$$D_{eff}=a\phi^b D_d \quad (15)$$

where $a=0.5$, $\varphi$=the corrected image porosity $\varphi_\infty$, $b=2$, and $D_d$ is the dominant pore throat size as determined from the non-wetting liquid capillary pressure curve.

The permeability image segmentation correction factor $\beta_S$ can be calculated from the image porosity $\varphi_I$ (obtained as disclosed above) and the measured porosity $\varphi_M$, which is obtained by physically measuring the porosity of the rock, in accordance with the following equation:

$$\beta_S=(\varphi_I/(\varphi_M))^3([1-\varphi_M]/[1-\varphi_I])^2 \quad (16).$$

$\beta_S$, however, provides only a very small correction, and, therefore, in the absence of a physical measurement of the porosity of the rock, $\beta_S$ may be assumed to be 1.

Once the permeability image resolution correction factor $\beta_R$, the permeability field of view correction factor $\beta_V$, and the permeability image segmentation correction factor $\beta_S$ are known or estimated, the corrected image permeability of the rock is obtained. The corrected image permeability of the rock may be obtained according to equation (8) above. The corrected image permeability of the rock is approximately equal to the true permeability of the rock as measured by physical measurements.

EXAMPLE

The following non-limiting example of an embodiment of the method of the present invention as claimed herein is provided for illustrative purposes only.

The corrected image permeability of twelve sandstone samples from separate hydrocarbon-containing formations was determined in accordance with the method of the present invention and was compared with the true permeability of the sandstones as determined by physical measurements.

Twelve core samples of sandstone were recovered from separate hydrocarbon-containing formations. The true permeability of each of the samples was determined in accordance with the industry standard of laminar flow brine injection into the samples.

Figure 4:
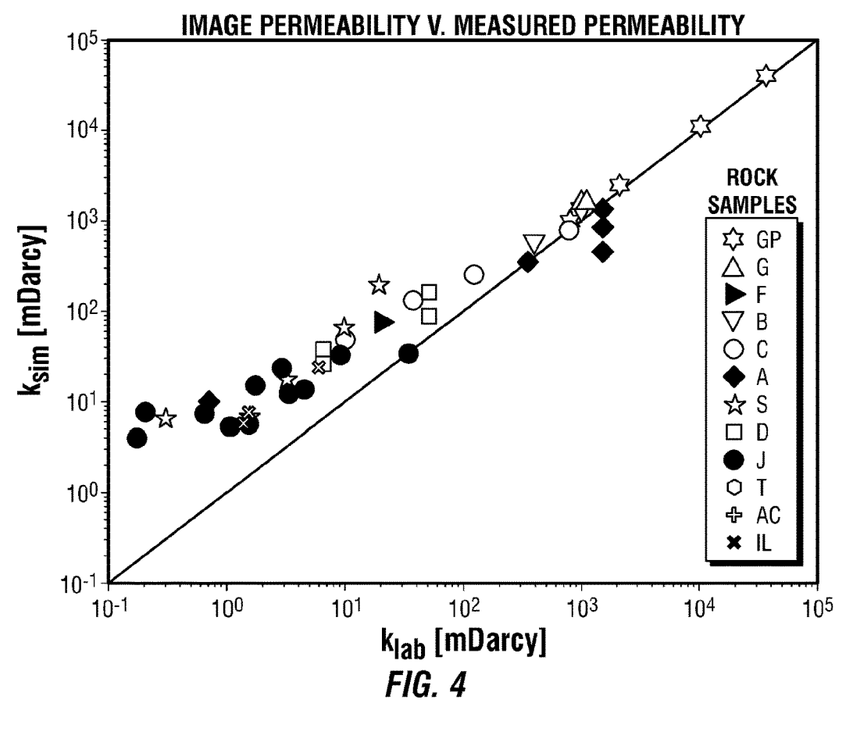
FIG. 4 is a graph showing a plot of laboratory measured permeability of rocks v. the image permeability as determined by digital rock image methods without applying image permeability correction factors.

The permeability of each of the sandstone samples was then estimated by digital rock imaging. Mini-plugs of each of the samples were extracted from the original cores. The mini-plug samples were three-dimensionally imaged by micro-CT imaging at ambient temperature. The mini-plug samples were scanned at one or more resolutions of 2.0 μm (e.g. 1 voxel of the image=2.0 μm³), 4.0 μm, and/or 8.0 μm. The resulting three-dimensional micro-CT images were then processed to segment each image into pore space voxels and solid material voxels using a Fuzzy C-Means clustering algorithm. The image permeability of each of the samples at each resolution was then estimated from the sample images assuming brine injection under a laminar flow regime. A graph of a plot of the true permeability of the samples relative to the computed image permeability is shown in FIG. 4. The image permeability provides a good representation of the true permeability when the plotted data falls on the x=y line, however, below 100 mDarcy the image permeability of the samples falls well above the x=y line indicating that the permeability was significantly overestimated under 100 mDarcy when derived from an image.

A mercury capillary injection curve similar to the curve shown in FIG. 2 was then plotted for each sample at each resolution from the segmented three-dimensional images of the rocks. An image-based curve was created by plotting the fractional bulk volume of a segmented rock image occupied by mercury against pressure in accordance with the Young-Laplace equation (P=4σ cos θ/D, P=pressure, D=pore throat size penetrated at a given pressure P, σ=the mercury liquid-air surface tension (480 dyne/cm), and θ=the contact angle (140°)) where voxels of pore space of pore bodies having a pore throat size of D or larger are assumed to be filled with mercury at the given pressure.

An image pore throat resolution parameter $N_I$ was determined for each digital rock sample at each resolution from its respective mercury capillary injection curve and the voxel size for each segmented three-dimensional image. The pore throat size entered by mercury at the entry pressure ($D_d$) was determined from the mercury capillary injection curve and the Young-Laplace equation utilizing the entry pressures where the entry pressure ($P_d$). The voxel size ($\Delta x$)

was the resolution of the image=2.0 µm, 4.0 µm, or 8.0 µm. The pore throat resolution parameter $N_I$ was determined from the equation $N_I=D_d/\Delta x$.

A pore geometric factor G was then determined for each sample at each respective resolution from the mercury capillary injection curves by curve fitting with a least square curve fitting, with higher weight given to pores that are better resolved in the image.

The image porosity of each of the digital rock samples at each resolution was determined from the segmented three-dimensional images of the rock by summing the number of voxels representing pore space in the segmented image and dividing by the total number of voxels in the image as determined from the imaging parameters. The pore throat resolution parameter $N_I$ and the pore geometric factor G were then used to determine an image porosity correction factor $\alpha$ according to the equation $\alpha=e^{-G/Log10(N)}$. The corrected image porosity was then determined for each of the mini-plug sample images at each resolution according to the equation $\varphi_I/\alpha=\varphi_\infty$.

Figure 5:
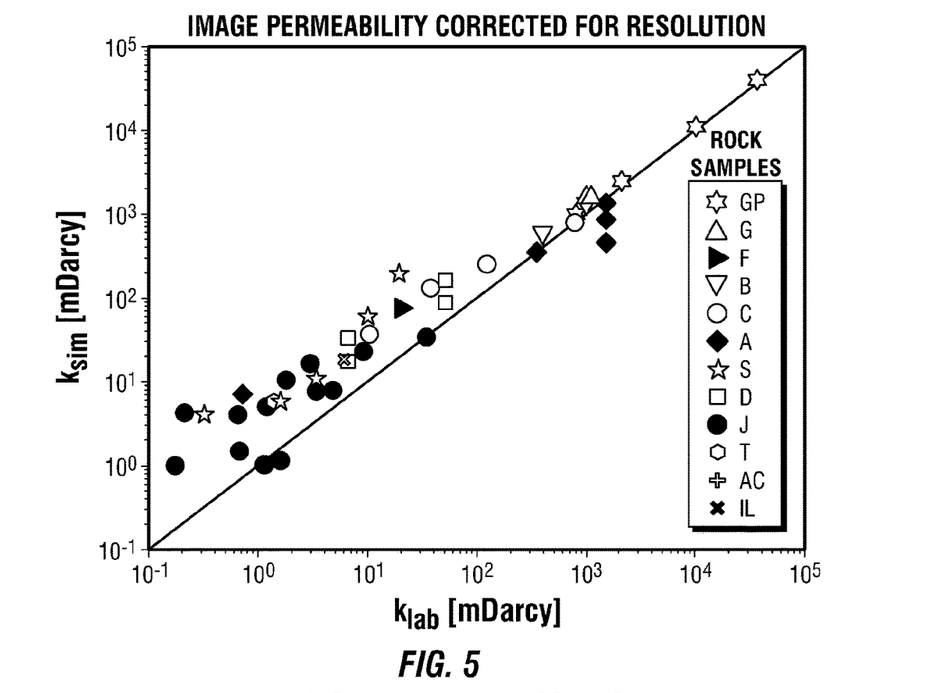
FIG. 5 is a graph showing a plot of laboratory measured permeability of rocks v. the image permeability as determined by digital rock image methods corrected by a permeability image resolution correction factor.

A permeability image resolution correction factor OR for each sample image at each resolution was determined by calculating $N_E$ in accordance with equation (11) above. The image permeability was then corrected using the calculated permeability image resolution factor according to the following equation: $k_\infty=k_I/\beta_R$. A graph of a plot of the true permeability of the samples relative to the computed image permeability corrected by the permeability image resolution correction factor is shown in FIG. 5, indicating that the image permeability was substantially corrected by the permeability image resolution correction factor, but was still overestimated under 100 mDarcy.

Figure 6:
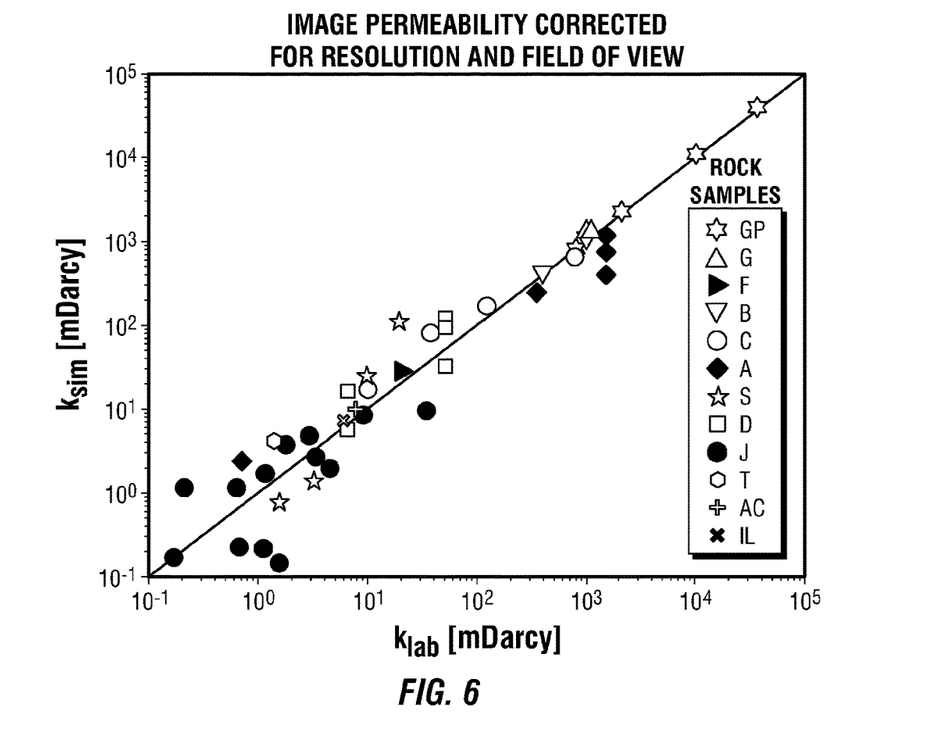
FIG. 6 is a graph showing a plot of laboratory measured permeability of rocks v. the image permeability as determined by digital rock image methods corrected by a permeability image resolution correction factor and a permeability field of view correction factor.

Each three-dimensional segmented image was further segmented using a watershed segmentation algorithm, and a permeability field of view correction factor $\beta_V$ for each resulting sample image at each resolution was then determined according to the equations (13) and (14) above from the corrected image porosity, the pore resolution parameter $N_I$, the dominant pore throat size $D_d$ determined from the mercury liquid capillary pressure curve, and $N_{REV}$ calculated as described above. The image permeability already corrected by the permeability image resolution correction factor was then further corrected using the calculated permeability field of view correction factor according to the following equation: $k_\infty=k_I/(\beta_R\beta_V)$. A graph showing a plot of the true permeability of the samples relative to the computed image permeability corrected by both the permeability image resolution correction factor OR and the permeability field of view correction factor $\beta_V$ is shown in FIG. 6. The graph indicates that the image permeability of the samples was further corrected and substantially matched the true permeability of the samples by the use of the permeability field of view correction factor in addition to the permeability image resolution correction factor to correct the image permeability.

Figure 7:
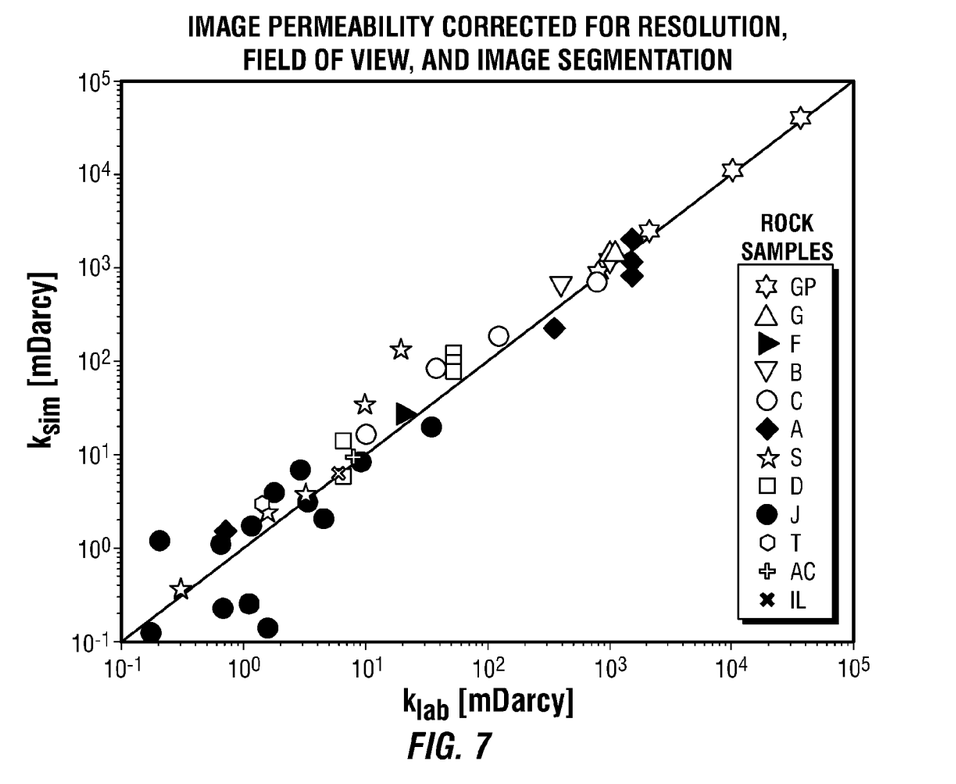
FIG. 7 is a graph showing a plot of laboratory measured permeability of rocks v. the image permeability as determined by digital rock image methods corrected by a permeability image resolution correction factor, a permeability field of view correction factor, and a permeability image segmentation correction factor.

A permeability image segmentation correction factor $\beta_S$ was determined for each of the sample images at each resolution. The true porosity of each of the samples was measured in accordance with the industry standard method of gas expansion using a helium porosimeter. The permeability image segmentation correction factor $\beta_S$ was then determined from the corrected image porosity and the measured true porosity in accordance with equation (16) above. A graph of a plot of the true permeability of the samples relative to the computed image permeability corrected by the permeability image resolution correction factor $\beta_R$, the permeability field of view correction factor $\beta_V$, and the permeability image segmentation correction factor $\beta_S$ calculated in accordance with equation (8) above is shown in FIG. 7. The graph indicates that the image permeability of the samples utilizing the permeability image segmentation correction factor $\beta_S$ in addition to the permeability image resolution correction factor $\beta_R$ and the permeability field of view correction factor $\beta_V$ was corrected slightly by reducing the scatter of the plotted permeabilities relative to the plotted permeabilities using only the permeability image resolution correction factor $\beta_R$ and the permeability field of view correction factor $\beta_V$ to correct the image permeability, however, the correction was not significant and use of just the permeability image resolution correction factor $\beta_R$ and the permeability field of view correction factor $\beta_V$ to correct the image permeability ($\beta_S=1$) provided sufficient correction to the image permeability to reasonably estimate the true permeability from the corrected image permeability.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

We claim:

1. A method for estimating the permeability of rock, comprising:

obtaining a three-dimensional image of a rock wherein the image is comprised of a plurality of voxels and the image has a resolution;

processing the three-dimensional image of the rock to segment the image by selecting each voxel of the image to represent either pore space in the rock or solid material in the rock;

estimating an image permeability of the rock from the segmented three-dimensional image of the rock;

deriving a non-wetting liquid capillary pressure curve from the segmented three-dimensional image of the rock;

determining one or more permeability correction factors from the segmented three-dimensional image and the non-wetting liquid capillary pressure curve; and applying the one or more permeability correction factors to the image permeability of the rock to obtain a corrected permeability of the rock.

2. The method of claim 1, wherein the three-dimensional image of the rock is obtained by x-ray computer tomography.

3. The method of claim 1, wherein the rock is obtained from a hydrocarbon-bearing formation comprised of sandstone, carbonate, shale and combinations thereof.

4. The method of claim 1, wherein the non-wetting liquid is mercury or Wood's metal.

5. The method of claim 1, wherein the image permeability of the rock is estimated by computation in a permeability simulation method utilizing the segmented three-dimensional image of the rock.

6. The method of claim 1, wherein the one or more permeability correction factors comprises a permeability image resolution correction factor that is determined from an image entry pore throat size, as determined from the non-wetting liquid capillary pressure curve, voxel size, as determined from the image resolution, and a predicted measured entry pore throat size to voxel size ratio.

7. The method of claim 1, wherein the one or more permeability correction factors comprises a permeability image field of view correction factor that is determined from the non-wetting liquid capillary pressure curve, the voxel size in the image, the number of voxels along an axis extending the length, width, or height of the image, and a corrected image porosity estimated from the segmented three-dimensional image of the rock and the non-wetting liquid capillary pressure curve.

8. The method of claim 1, wherein the non-wetting liquid capillary pressure curve is derived from the segmented three-dimensional image of the rock at pressures of up to an image-limited pressure, where the image-limited pressure is the minimum pressure that can be applied on the non-wetting liquid to overcome the capillary pressure of the narrowest pore throat distinguishable from the segmented three-dimensional image of the rock.

9. The method of claim 1, wherein the one or more permeability correction factors comprises a pore geometric factor is determined from the non-wetting liquid capillary pressure curve by plotting a best fit curve to the non-wetting liquid capillary pressure curve and determining the pore geometric factor from the shape of the curve.

10. The method of claim 1 wherein the one or more permeability correction factors comprises a pore throat resolution parameter is determined by determining a pore throat size of pores entered by the non-wetting liquid at an entry pressure from the non-wetting liquid capillary pressure curve and calculating a ratio between the pore throat size of pores entered by the non-wetting liquid at the entry pressure and the resolution of the image.

11. The method of claim 1, wherein the three-dimensional image is obtained from a cloud-based tool adapted to store and process 2D projection images from a pore-scaling imaging technology.

12. A backpropagation-enabled method for estimating the permeability of rock from a three-dimensional image of rock, comprising the steps of:

obtaining a three-dimensional image of rock, the three-dimensional image having a resolution;

applying a backpropagation-enabled trained model to segment the three-dimensional image of rock;

estimating an image permeability of the rock from the segmented image;

deriving a non-wetting liquid capillary pressure curve from the segmented image;

determining one of more permeability correction factors from the non-wetting liquid capillary pressure curve and the resolution; and applying the one or more permeability correction factors to the image permeability of the rock to obtain a corrected permeability of the rock.

13. The method of claim 12, wherein the trained model is produced by:

providing a training set of images of rock;

segmenting the images of rock into a plurality of labeled voxels, the plurality of labeled voxels representing pore spaces and solid material in the rock; and using the labeled voxels to train a model via backpropagation.

14. The method of claim 13, wherein the training set of images is obtained from a cloud-based tool adapted to store and process 2D projection images from a pore-scaling imaging technology.

15. The method of claim 12, wherein the non-wetting liquid capillary pressure curve is derived from the segmented image at pressures of up to an image-limited pressure, where the image-limited pressure is the minimum pressure that can be applied on the non-wetting liquid to overcome the capillary pressure of the narrowest pore throat distinguishable from the segmented image of the rock.

16. The method of claim 12, wherein the three-dimensional image is obtained from a cloud-based tool adapted to store and process 2D projection images from a pore-scaling imaging technology.

* * * * *